(12) United States Patent
Dhupar

(10) Patent No.: US 10,327,861 B2
(45) Date of Patent: Jun. 25, 2019

(54) SURGICAL IMPLANT ALIGNMENT DEVICE

(71) Applicant: Straight Shot, LLC, Windsor, CO (US)

(72) Inventor: Scott Kailash Dhupar, Windsor, CO (US)

(73) Assignee: Straight Shot, LLC, Windsor, CO (US)

( * ) Notice: Subject to any disclaimer, the term of this patent is extended or adjusted under 35 U.S.C. 154(b) by 273 days.

(21) Appl. No.: 15/331,308

(22) Filed: Oct. 21, 2016

(65) Prior Publication Data

US 2017/0112586 A1  Apr. 27, 2017

Related U.S. Application Data

(60) Provisional application No. 62/245,015, filed on Oct. 22, 2015.

(51) Int. Cl.
| | | |
|---|---|---|
| *A61B 90/13* | (2016.01) | |
| *A61B 90/35* | (2016.01) | |
| *A61B 17/80* | (2006.01) | |
| *A61B 34/20* | (2016.01) | |
| *A61B 90/00* | (2016.01) | |

(52) U.S. Cl.
CPC ............ *A61B 90/13* (2016.02); *A61B 17/808* (2013.01); *A61B 90/35* (2016.02); *A61B 2034/2068* (2016.02); *A61B 2090/366* (2016.02)

(58) Field of Classification Search
CPC . A61B 2017/681; A61B 17/808; A61B 17/88; A61B 17/8872; A61B 17/8875; A61B 17/8894; A61B 2017/90; A61B 90/13; A61B 90/35
See application file for complete search history.

(56) References Cited

U.S. PATENT DOCUMENTS

| | | | |
|---|---|---|---|
| 5,141,512 A | 8/1992 | Farmer et al. | |
| 5,606,590 A | 2/1997 | Petersen et al. | |
| 6,167,145 A | 12/2000 | Foley et al. | |

(Continued)

FOREIGN PATENT DOCUMENTS

| | | |
|---|---|---|
| CN | 202191369 | 4/2012 |
| WO | WO2009/043118 | 4/2009 |

OTHER PUBLICATIONS

International Search Report and Written Opinion regarding PCT/US2016/058194 dated Mar. 31, 2017.

*Primary Examiner* — Christian A Sevilla
(74) *Attorney, Agent, or Firm* — Schneider IP Law LLC; Laura A. Schneider

(57) ABSTRACT

An alignment device for aligning an orthopedic plate with a bone attachment site includes one or more one light sources that are secured to an orthopedic plate holder with a mounting interface and in a location spaced from the orthopedic plate that is releasably secured to the distal end of the plate holder. The light sources are configured to project an illuminated indication pattern onto the plane the orthopedic plate and aligned with the primary axis of interest of the orthopedic plate, and which indication pattern extends a sufficient lateral distance away from the plate holder to allow the medical professional to align the axis of interest of the orthopedic plate with an out-of-view bone attachment site using at least one superficial anatomic landmark on the exterior of the patient and remote from the bone attachment site.

30 Claims, 15 Drawing Sheets

(56) References Cited

U.S. PATENT DOCUMENTS

| | | |
|---|---|---|
| 6,236,875 B1 | 5/2001 | Bucholz et al. |
| 6,348,058 B1 | 2/2002 | Melkent et al. |
| 6,743,235 B2 | 6/2004 | Subba Rao |
| 8,388,627 B2 | 3/2013 | Panchbhavi |
| 8,974,468 B2 | 3/2015 | Borja |
| 2005/0070897 A1 | 3/2005 | Petersen |
| 2006/0184177 A1 | 8/2006 | Echeverri |
| 2007/0043375 A1 | 2/2007 | Anissian |
| 2007/0073296 A1 | 3/2007 | Panchbhavi |
| 2009/0234360 A1 | 9/2009 | Alexander |
| 2010/0145337 A1 | 6/2010 | Janna et al. |
| 2010/0198275 A1 | 8/2010 | Chana et al. |
| 2010/0249782 A1* | 9/2010 | Durham .................. A61B 5/06 606/62 |
| 2011/0106092 A1 | 5/2011 | Fisher et al. |
| 2011/0270319 A1 | 11/2011 | Sheffer |
| 2012/0290019 A1 | 11/2012 | Chellaoui |
| 2014/0276000 A1 | 9/2014 | Mullaney et al. |
| 2014/0276889 A1 | 9/2014 | Head et al. |

\* cited by examiner

SURGICAL IMPLANT ALIGNMENT DEVICE

RELATED APPLICATIONS

This application claims the benefit of U.S. Provisional Patent Application No. 62/245,015, filed Oct. 22, 2015, and entitled "Surgical Implant Alignment Guide," which application is incorporated by reference in its entirety herein, and for all purposes

FIELD OF THE INVENTION

The present invention generally relates to methods and devices for positioning and aligning orthopedic implants with bone attachment sites during surgery.

BACKGROUND

Surgeons have techniques and implants to perform stable internal fixation of the human body. Current technology has the ability to stabilize fractures or to securely attach implants to bones in the case of elective or emergent medical conditions. However, when surgery is performed, there is limited visualization of a bone in a surgical field (i.e., most of the bone is still covered by skin and other soft tissues). This is partially intentional (in the case of minimally invasive surgery) and partially due to the nature of surgical technique. Surgeons intentionally try to minimize surgical exposure to avoid iatrogenic injury to soft tissues, to avoid devascularization, and to minimize post-operative recovery for patients. Due to these reasons, the limited amount of exposed bone makes it difficult to judge the alignment of an implant on the full length of the bone. Consequently, it is difficult for a surgeon to apply an implant perfectly collinear to the bone. This becomes evident only after surgery, when x-rays are taken and it is shown that the implant is not aligned collinear with the bone. The difficulty to align a plate to a bone is equally applicable to bones of the upper extremities, lower extremities, and spine. It is also applicable to surgical technique in human beings, dogs, cats, horses, goats, sheep, cattle, pigs, and the like.

Consequently, a need exists for an alignment apparatus or device that facilitates the accurate alignment of an orthopedic implant to a bone attachment site that is at least partially out-of-view of the surgeon. It is toward such an alignment device that the present disclosure is directed.

SUMMARY

Briefly described, one embodiment of the present disclosure comprises an surgical implant alignment device that is securable to an orthopedic plate holder for aligning an orthopedic plate with a bone attachment site. The orthopedic plate holder generally includes a distal end that is releasably attachable to an orthopedic plate in a fixed angular position to define a plane of interest and a predetermined axis of interest of the orthopedic plate within the plane of interest, and a proximal end that is adapted for holding by a medical professional.

The alignment device generally includes one or more light sources that are configured to project an illuminated indication pattern onto the plane of interest of the orthopedic plate, and that is also aligned with the predetermined axis of interest of the orthopedic plate. The alignment device also includes a mounting interface that is configured to secure the light source to the orthopedic plate holder in a location spaced from the distal end, in a fixed angular position relative to the plate holder, and to maintain the angular relationship between the light source and the orthopedic plate as the distal end of the orthopedic plate holder is inserted into a patient by a medical professional and moved toward a bone attachment site that is at least partially out-of-view. In addition, the illuminated indication pattern extends a sufficient lateral distance away from the orthopedic plate holder and has a substantially constant brightness along the length thereof that allows the medical professional to align the axis of interest of the orthopedic plate with the out-of-view bone attachment site using one or more superficial anatomic landmarks on the exterior of the patient and that are remote from the bone attachment site.

Another embodiment of the present disclosure comprises an implant placement and alignment system for positioning and aligning an orthopedic implant to a bone attachment site. The system includes an implantation tool having a distal end that is releasably attachable to an orthopedic implant in a fixed angular position to define a plane of interest of the orthopedic implant and a predetermined axis of interest of the orthopedic implant within the plane of interest, and a proximal end that is adapted for holding by a medical professional. The system also includes an alignment device that is securable to the implantation tool for aligning the predetermined axis of interest of the orthopedic implant with the bone attachment site prior to fixation.

The alignment device further includes one or more light sources that are configured to project an illuminated indication pattern onto the plane of interest of the orthopedic implant and aligned with the predetermined axis of interest of the orthopedic implant, and a mounting interface that is configured to secure the light sources to the implantation tool in a location spaced from the distal end, in a fixed angular position relative to the implantation tool, and to maintain the angular relationship between the light sources and the orthopedic plate as the distal end of the implantation tool is inserted into a patient by a medical professional and moved toward a bone attachment site that is at least partially out-of-view. Moreover, the illuminated indication pattern extends a sufficient lateral distance away from the implantation tool to allow the medical professional to align the axis of interest of the orthopedic plate with the out-of-view bone attachment site using a plurality of superficial anatomic landmarks on the exterior of the patient and remote from the bone attachment site.

Yet another embodiment of the present disclosure comprises a method for mounting an orthopedic plate to a bone attachment site using a plate holder having a proximal end that is adapted for holding by a medical professional, a distal end, an orthopedic plate secured to the distal end in a fixed angular position to define a plane of interest of the orthopedic plate and a predetermined axis of interest of the orthopedic plate within the plane of interest, and an alignment device having a light source secured to the plate holder in a location spaced from the distal end. The method generally includes using the light source of the alignment device to project an illuminated indication pattern onto the plane of interest of the orthopedic plate and that is aligned with the predetermined axis of interest of the orthopedic plate, and then moving the plate holder to insert the orthopedic plate into a patient and adjacent to a bone attachment site that is out-of-view of the medical professional. The method also includes rotating the plate holder to align the illuminated indication pattern with one or more superficial anatomic landmarks that are visible or palpable to the medical professional on the outer surface of the patient and remote from the bone attachment site, and thereby positioning the orthopedic plate in a desired collinear orientation relative to the out-of-view bone attachment site. The method further includes attaching the orthopedic plate to the bone attachment site, generally through fixation with bone screws, and then releasing the plate holder from the orthopedic plate and removing the plate holder from the patient.

The invention will be better understood upon review of the detailed description set forth below taken in conjunction with the accompanying drawing figures, which are briefly described as follows.

Those skilled in the art will appreciate and understand that, according to common practice, various features and elements of the drawings described above are not necessarily drawn to scale, and that the dimensions of the various features and elements may be expanded or reduced to more clearly illustrate the embodiments of the present disclosure described therein.

DETAILED DESCRIPTION

The following description, in conjunction with the accompanying drawings described above, is provided as an enabling teaching of exemplary embodiments of an orthopedic implant alignment device, or alignment device, and one or more methods for using the alignment device to accurately position and align an orthopedic implant with a bone attachment site that can be partially out-of-view of the surgeon. As described below, the alignment device can provide several significant advantages and benefits over other systems and devices for positioning and aligning orthopedic implants with a bone attachment site. However, the recited advantages are not meant to be limiting in any way, as one skilled in the art will appreciate that other advantages may also be realized upon practicing the present disclosure.

Furthermore, those skilled in the relevant art will also recognize that changes can be made to the described embodiments while still obtaining the beneficial results. It will further be apparent that some of the advantages and benefits of the described embodiments can be obtained by selecting some of the features of the embodiments without utilizing other features, and that features from one embodiment may be combined with features from other embodiments in any appropriate combination. For example, any individual or collective features of method embodiments may be applied to apparatus, product or system embodiments, and vice versa. Accordingly, those who work in the art will recognize that many modifications and adaptations to the embodiments described are possible and may even be desirable in certain circumstances, and are a part of the disclosure. Thus, the present disclosure is provided as an illustration of the principles of the embodiments and not in limitation thereof, since the scope of the invention is to be defined by the claims.

Figure 1:
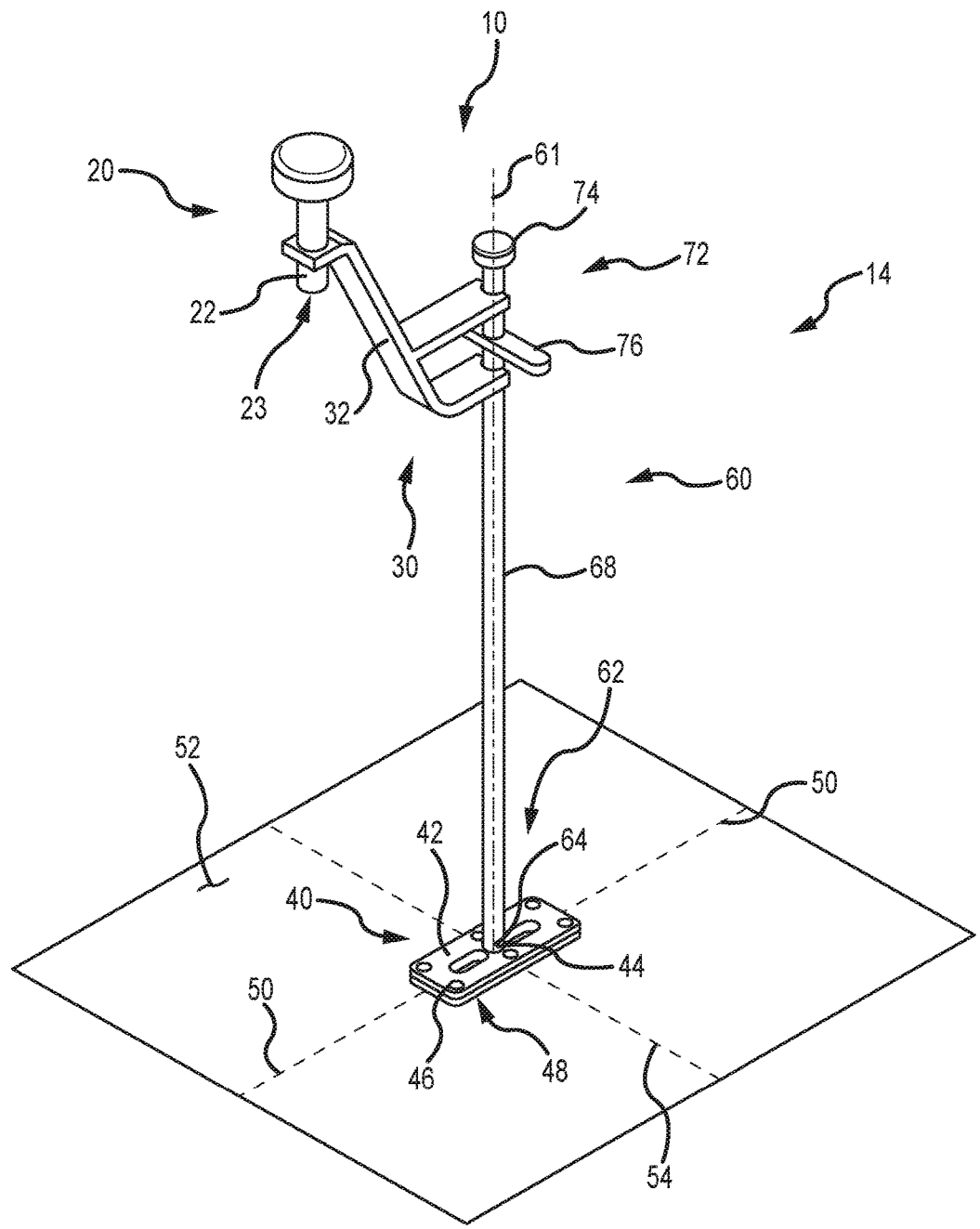
FIG. 1 is a perspective view of an implant alignment device secured to an orthopedic plate holder, in accordance with a representative embodiment of the present disclosure.
Figure 2:
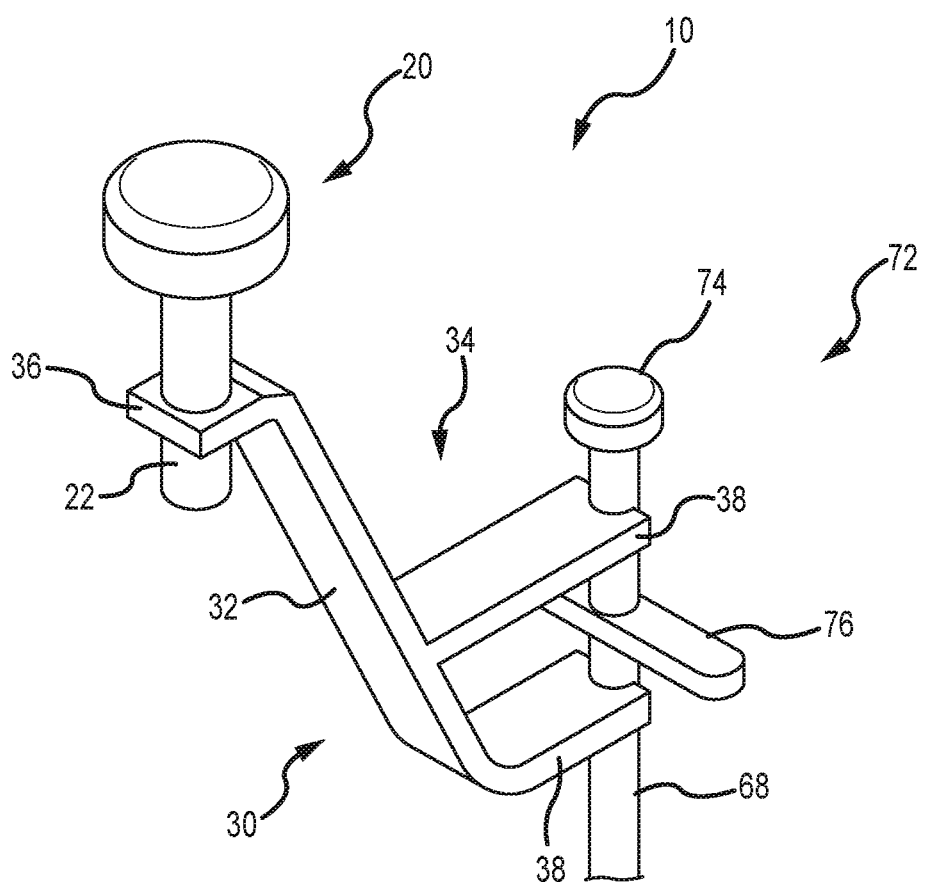
FIG. 2 is a close-up view of the implant alignment device of FIG. 1.

Referring now in more detail to the drawing figures, wherein like parts are identified with like reference numerals throughout the several views, FIGS. 1-2 illustrate one embodiment of an surgical implant alignment device 10 that can be used to align an orthopedic plate or implant 40 with a bone attachment site (not shown). The implant alignment device 10 generally includes one or more light sources 20 that are spaced a distance from the implant 40, and that are angularly secured and/or referenced to a predetermined or primary axis 50 of the implant 40. The spatial and angular positioning of the implant alignment device 10 can be accomplished via an implantation tool 60 to which the implant 40 can be removably secured, as well as a mounting interface 30 that secures the light source(s) to the implantation tool 60 at a location that is remote to the implant 40. In this way the light source(s) 20 can be activated before or after insertion of the implant 40 into the body of the patient, and are configured to project an illuminated indication pattern onto the outer surface of the patient that enables a medical professional or surgeon to align the implant 40 to the subcutaneous bone attachment site using markers or features that are visible to the surgeon on the outer surface of the patient.

The implant alignment device 10 of the present disclosure can allow the surgeon to effectively judge the placement of an implant, such as an orthopedic plate, relative to the full length of the bone or the anatomy in question. Instead of relying on the limited exposure of the surgical field, the surgeon can more reliably use the entire superficial anatomy to judge appropriate placement of the deep implant. In one aspect the surgeon may also choose to palpate specific superficial anatomic landmarks that predictably align with deep structures, and then mark the anatomic landmarks to create one or more visible reference markers on the exterior of the patient and remote from the bone attachment site to use as alignment reference points. Thus, the system of the present disclosure can be used to assist surgeons in placing implants (particularly plates) collinearly on bones using light beams and unique combinations of superficially palpable anatomic landmarks.

It will be appreciated that the present disclosure may not aid the surgeon in anatomically aligning the bones if the bones are not already in a grossly desired anatomic position. Generally, surgeons use distraction techniques, temporary fixation, and fluoroscopic visualization, among other methods, to gain anatomic alignment prior to placement of plate fixation. Plates are generally not used as a means to gain gross anatomic alignment. However, screws (with plates) are used to reduce bone fragments to the plate, to compress bone fragments, and to create buttress technique. These methods can be used by the surgeon to gain minor improvements in anatomy. The present disclosure is not intended to add to or detract from those commonly employed methods.

As shown in the FIGS. 1-2, the implantation tool to which the implant alignment device 10 is attached can be an orthopedic plate holder 60 comprising an hollow elongate rod 68 having a distal end 62 and a proximal end 72, with the implant or orthopedic plate 40 being releasably attached to the distal end 62 of the plate holder 60 through a coupling interface 64 associated with the plate holder 60, a coupling interface 44 associated with the plate 40, or both. For example, in one aspect the coupling interface 64 of the plate holder 60 can be a set of actuatable pinchers that grasp around a strut or structural member that defines the coupling interface 44 of the plate 40. The actuation of the coupling interface 64 can be accomplished through manipulation of an actuator handle 76 at the proximal end 72 of the elongate rod 60 near the handgrip 74, and which is connected to the coupling interface via a linkage that is positioned within the hollow rod 68. The present disclosure is not limited to any particular implant alignment device or type of coupling interface between the plate holder 60 and the orthopedic plate 40, however, and it will be appreciated that a wide variety of plate holders and coupling interfaces 44, 64 associated with the plate 40 and/or the plate holder 60 can be used to releasably coupled the plate 40 to the distal end 62 of the plate holder 60.

Moreover, and regardless of the type of coupling interface, the orthopedic plate or implant 40 can be releasably attached to the distal end 62 of the plate holder 60 in a fixed angular position that defines a predetermined or primary axis of interest 50, and in some embodiments a plane of interest 52 as well. In one aspect the axis of interest 50 of the plate 40 can generally correspond to the orthopedic plate's long axis that is intended to align with the long axis of the bone. It is contemplated, however, that in some embodiments the axis of interest 50 may not correspond to the long axis of the orthopedic plate. For orthopedic plates 40 that are generally planar and flat, such as that shown in FIG. 1, the plane of interest 52 can correspond to either the top surface 42 of the plate 40 or the bottom surface 48 that contacts the bone of the patient, especially when the plate 40 is attached to the plate holder 60 in an orientation that is perpendicular to the longitudinal centerline axis 61 of the elongate rod 68 of the plate holder, as shown in FIG. 1. And in situations where the plate is curved or sculpted to match the contour of the bone at the bone attachment site, a plane of interest 52 can generally be described as the plane defined by a flat surface upon which the plate may be resting prior to attachment to the plate holder 60, and that can also be perpendicular to the longitudinal centerline axis 61 of the elongate rod 68 after attachment to the plate holder 60.

The orthopedic plate 40 can also include a secondary axis of interest 54 that is transverse to the primary axis of interest 50. In some embodiments, such as that shown in FIG. 1, the secondary axis of interest 54 can be perpendicular to the primary axis of interest 50 and can intersect with the primary axis of interest 50 at the coupling point between the orthopedic plate 40 and the plate holder 60. However, in other aspects (not shown) the secondary axis of interest 54 can intersect with the primary axis of interest 50 at a non-right angle and at a location that is laterally spaced from the distal end 62 of the plate holder 60, so as to provide additional flexibility in aligning the orthopedic plate or implant 40 with the bone attachment site.

In the embodiment of the surgical implant alignment device 10 shown in FIGS. 1-2, the one or more light sources 20 can be a single light emission device, such as a highly-focused LED light or a laser 22, that is capable of producing, projecting, or emitting one or more light beams 24 that can form a straight line of light or a pattern of light lines within the plane of interest 52 of the orthopedic plate 40 attached to the distal end 62 of the plate holder 60. In addition, the projected straight line of light or a pattern of light lines can be aligned with the predetermined axis of interest 50 of the implant or orthopedic plate 40.

It will be appreciated that the light source 20 can be any of a variety of light sources, such as a laser, metal halide light, fluorescent light, high-pressure sodium light, incandescent light or LEDs (light emitting diode), or a device to focus visible light, is operably coupled or attached to the plate holder 60 with the mounting inter face 30. In addition, the housing of the light source 20 could be composed of plastic, metal, or any like material and would be sterilized by a manufacturer prior to use in the operating room. In one aspect the emission of laser or light from the light emitting device can be triggered by the surgeon when he or she is ready to use the laser during surgery. Moreover, the source of energy to power the laser can be a battery (energy storage) or wire (energy delivery) from a power source.

Figure 3:
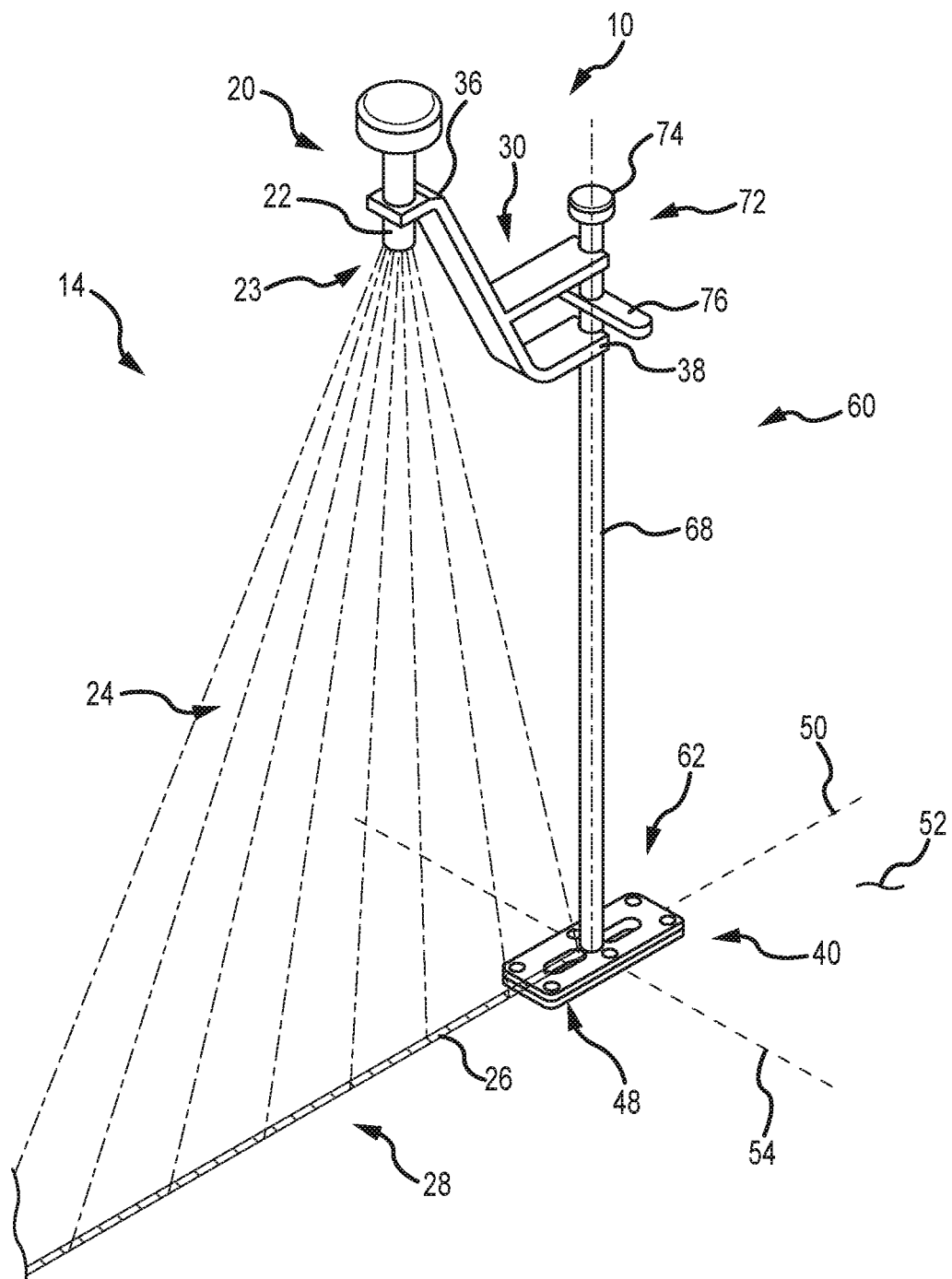
FIG. 3 is another a perspective view of the implant alignment device of FIG. 1 projecting an illuminated indication pattern onto the plane of interest of an orthopedic plate attached to the distal end of the plate holder.

The light source 20 can further include one or more light-directing or optical devices 23, such as lenses, mirrors and the like, at an output end for shaping the beam of light 24 into a flattened and expanding triangular shape that forms a single straight light line 26 upon contact with any physical object in its path (FIG. 3). If desired, a single light source 20 can be configured to project a single light line 26, as shown in the drawing, or multiple light lines, with the light line or lines projecting from the light source defining an illuminated indication pattern 28. Moreover, the illuminated indication pattern 28 can be any form of pattern useful for aligning the implant or orthopedic plate 40 with one or more reference markers exterior to the patient and remote from the bone attachment site, including but not limited to a straight line, a cross hair pattern, and a grid pattern.

As discussed in more detail below, in one aspect these reference markers can be superficial anatomic structures on a body that may act as landmarks for the alignment of an orthopedic plate with bone structures deeper within the body, as well as visible marks made with a skin marker on the skin directly above the underlying anatomic landmark. In other aspects the reference markers could be any marked location on the body of the patient, with or without an underlying anatomic structure, or any location in the surrounding environment (e.g. a table, a wall, or target device in the operating room), that can serve as a remote marking site for aligning the illuminated indication pattern 28 with the bone attachment site.

In addition, while using an ink-based skin marker may be a preferred technique for creating a reference marker on the skin or protective covering, other forms of marking and types of markers are also possible and considered to fall within the scope of the present disclosure. For instance, reflective or fluorescent tapes, adhesive stickers, liquid inks and the like can be used to create reference markers that interact with the beam of light 24 from the light source 20 to create a stronger visible indication when alignment has been achieved. Various types of targets, both non-active and electronic, can be also attached to straps or brackets or otherwise coupled to the patient's body at the anatomic location to establish the reference markers aligning the illuminated indication pattern 28.

The light source 20 is operably coupled to the orthopedic plate holder 60 with a mounting interface 30, and at a location sufficiently spaced from the distal end 62 of the plate holder 60 so as to remain external to the patient after the distal end 62 and attached orthopedic plate 40 have been inserted into the patient. In the embodiment of the surgical implant alignment device 10 shown in FIGS. 1-2, the mounting interface 30 can comprise a light mounting bracket 32 having a base portion 34, a light mounting element 36, and a plate holder mounting element 38. The light mounting element 36 can provide the structure for holding or attaching the light source 20 to the light mounting bracket 32, while the plate holder mounting element 38 can provide the structure for operably attaching the light mounting bracket 32 to a plate holder 32. In addition, a variety of configurations and materials may be used for making different portions of the light mounting bracket 32. For example, the base 34 may be made of one or more metals such as titanium, aluminum or steel, as well as various forms of plastics, depending upon the specific type of applications for the implant alignment device 10 as well as the specific type of plate holder 60 to which the light mounting bracket 32 will be attached.

In one aspect one or both of the light mounting element 36 and the plate holder mounting element 38 can provide for angular or rotational adjustment of the attached element (i.e. light source 20 or plate holder 60) relative to the base portion 34 of the light mounting bracket 32. For example, the light mounting element 36 can provide for rotation of the light source relative 20 to the base portion 34 so as to bring a projected light line into contact with the distal end 62 of the plate holder 60. In a similar fashion, the plate holder mounting element 38 can provide for angular or rotational adjustment of the entire implant alignment device 10 relative to the longitudinal centerline axis 61 of the elongate rod 68 of the plate holder 60, so as to bring the projected illuminated indication pattern 28 of line 26 into alignment with the predetermined axis of interest 50 of the orthopedic plate 40 that is releasably attached or coupled to the distal end 62 of the plate holder 60.

Although shown in FIGS. 1-2 as being separable from both light source 20 and plate holder 60, the mounting interface 30 can also be formed integral with the plate holder 60 or implantation tool. For instance, the light mounting bracket 32 may be cast together with the elongate rod 68 of the plate holder 60, so as to form a single integral supporting structure into which the other components, such as an actuator 76 for the plate holder 60 or the light source 20, can be mounted.

With reference to FIGS. 1 and 3, the implant alignment device 10 and the implantation tool or orthopedic plate holder 60 can together form an implantation system 14 for inserting, positioning, and aligning an orthopedic plate or implant 40 to a bone attachment site. In the illustrated embodiment the light source 20, such as LED 22, can project a thin, triangularly-shape (i.e. expanding) beam of light 24 that forms a straight light line 26 upon contact with a physical object in its path, and which light line 26 can intersect with the distal end 62 of the plate holder 60 in one direction and extend laterally or radially away from the plate holder 60 in the opposite direction to defined an illuminated indication pattern 28 comprised of the single light line 26. In addition, the implant alignment device 10 and the orthopedic plate holder 60 can be coupled or arranged together so that the illuminated indication pattern 28 aligns with the primary axis of interest 50 of the orthopedic plate 40 prior to insertion of the orthopedic plate into the body.

Depending the distance between the implant alignment device 10 and the distal end 62 of the plate holder 60, as well as the angle of expansion provided of the beam of light 24 by the optical device 23 at the output end of the light source 20, the light line 26 projected by the light source 20 can be configured to extend a substantial lateral (i.e. radial) distance away from the plate holder 60 to facilitate alignment with reference markers or anatomical features that are some distance away from the bone attachment site for the implant 40. For instance, the light line 26 can be configured to project laterally (i.e. radially) away from the plate holder 60 at least two, three and even four times the length of the elongate rod 68 of the orthopedic plate holder 60, which can generally be 10 to 12 inches in length. In other aspects the light line 26 can be configured to project laterally up to 3 feet, or 36 inches, or more away from the plate holder. In addition, the light line 26 can have a substantially constant brightness along its entire length, and its brightness can be sufficient to be readily visible in the highly illuminated operating room setting.

The lateral projection distance of the light line 26 away from the bone attachment site can allow the operator, (in most cases the surgeon) to accurately judge the alignment of the implant in the longitudinal plane of the body. If the implant or plate is positioned inaccurately, then the extreme end of the light beam will be positioned far from the expected surface anatomy or reference marker and easily judged by the operator to be off target, since a small angular misalignment of the implant 40 at the bone attachment will be amplified into a large angular displacement from the anatomical or reference marker at the extreme end of the light line 26. If the extreme end of the light line 26 is on target with the surface anatomy of the bone(s) in question, then the surgeon can confidently judge the implant to also be collinear to the bone that is deep within the soft tissue.

For example, in the tibia, the tibial tubercle is commonly considered the center of the proximal end of the anterior tibia while the mid-point of the ankle joint is considered the center of the distal end of the anterior tibia. If one end of a continuous light line is on the tibial tubercle and the other end in on the mid-point of the ankle, then the surgeon can be confident that the plate is collinear to the tibia. Another example; in the cervical spine, after stabilizing rotation of the neck in a neutral position, if one end of the continuous light line is at the center of the patient's forehead, while the other end is at the center of the sternal notch, then the surgeon can feel confident that they are collinear to the cervical spine.

The following examples are provided to illustrate further the various applications and are not intended to limit the invention beyond the limitations set forth in the appended claims.

Example 1

Figure 4:
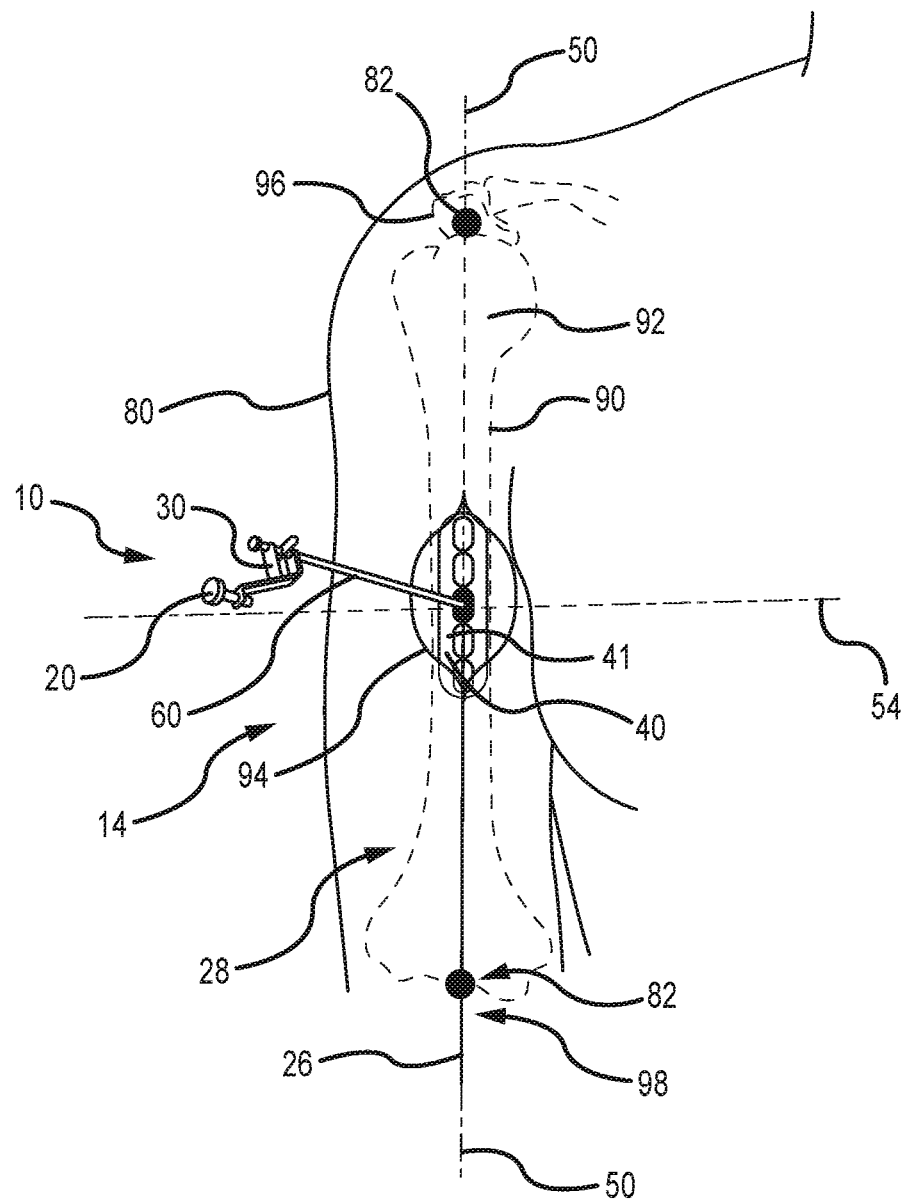
FIG. 4 is a schematic diagram illustrating the application of the implant alignment device of FIG. 1 in aligning an orthopedic plate to the anterior humerus of a patient, in accordance with another representative embodiment of the present disclosure.

FIG. 4 illustrates an embodiment of the implant alignment device 10 and implantation system 14 of the present disclosure as may be applied to align an orthopedic plate 40 to the humerus 90 of a patient. As shown in the drawing, a limited exposure of the typical anterior humerus 92 is provided through a typical anterior incision 94 on the upper arm 80. The surgeon may palpitate and/or mark anatomic structures 96, 98 using a skin marker to create superficial anatomic landmarks or reference markers 82 on the exterior of the patient and remote from the bone attachment site.

The surgeon or an assisting medical professional can also attach the orthopedic plate 40 to the distal end of the plate holder 60 and activate the light source 20 of the implant alignment device 10 to verify that the illuminated indication pattern 28 is aligned with the primary axis of interest 50 of the orthopedic plate. In situations where the illuminated indication pattern 28 is not aligned with the primary axis of interest 50 and angular or rotational adjustment of the implant alignment device 10 relative to the bone holder 60 is possible, the angular position of the implant alignment device 10 can be adjusted to bring the illuminated indication pattern 28 into alignment with the primary axis of interest 50.

During surgery the distal end of the implantation system 14 can then be used to insert the plate 40 into the incision 94 and adjacent the desired bone attachment site, and the light source 20 can be activated to project an illuminated indication pattern 28 that extends from the distal end of the plate holder to one or both of the reference markers 82 on the exterior of the patient. The surgeon can then align the illuminated indication pattern 28 emitted by the light source 20 of the implant alignment device 10 with these marked superficial anatomic structures 96, 98 to aid in maintaining position. In embodiments where the implant alignment device 10 includes a single light source 20 that projects an illuminated indication pattern 28 comprising a single light line 26 aligned with the primary axis of interest 50 of the orthopedic plate 40, the light line 26 may be aligned with either of the reference markers 82.

In another aspects where the implant alignment device 10 projects a single radially-extending light line 26 from the plate holder, the surgeon could also palpitate and/or mark two superficial anatomic landmarks that are located on the same side of the bone attachment site. In this scenario one of the superficial anatomic landmarks or reference markers can be closer to the bone attachment site while the other is more remote, and which together can be used to accurately align the illuminated indication pattern 28 with the bone attachment site to facilitate collinear alignment of the primary axis of interest 50 of the orthopedic plate 40 with the deep bone structure.

As discussed in more detail below, however, in other embodiments the implant alignment device can include multiple light sources that together project an illuminated indication pattern comprising multiple light lines that can be simultaneously aligned with multiple markers 82 for more accurate placement and alignment of the orthopedic plate 40. For example, the center of the acromion 96 and the tendon of the biceps brachii 98 are superficial structures that are centered at the ends of the humerus 90. If the surgeon palpitates these structures, marks them with a skin marker to create reference markers 82, and aligns the primary axis of interest 50 of an anterior humeral orthopedic plate 41 to both of these marked points 82 using the implantation system of the present disclosure, the doctor may be confident that the plate 41 is aligned collinearly to the typical anterior humerus 92.

The plate holder 60 can be firmly attached to the plate 41 using the plate manufacturer's attachment mechanism, and the light source 20 included in implant alignment device 10 can project the illuminated indication pattern 28 onto the skin overlying the hidden humerus 90. Now the surgeon can confidently attach the plate to the surface of the anterior humerus 92 with consistently good radiographic results.

Figure 5:
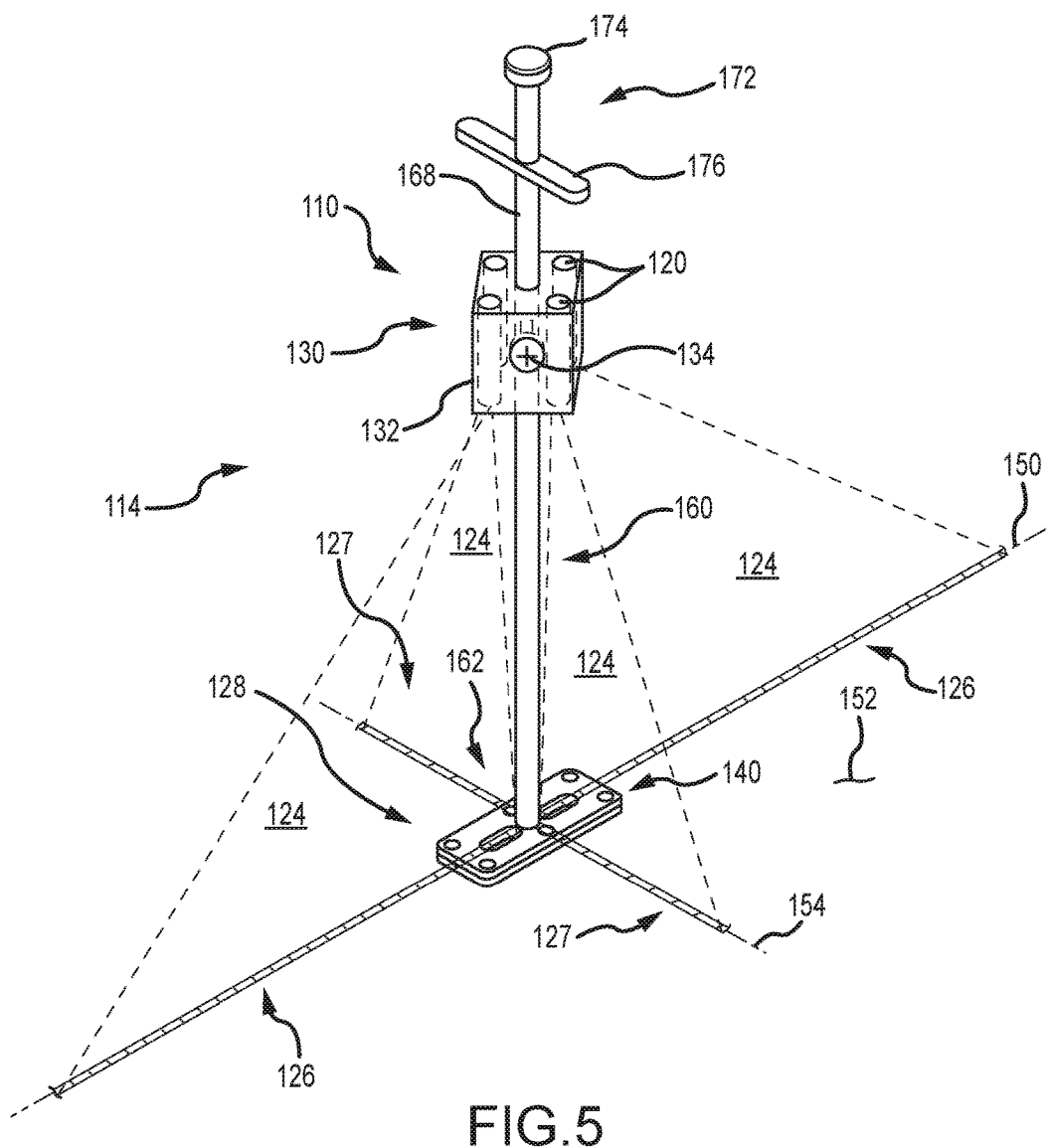
FIG. 5 is a perspective view of another implant alignment device projecting an illuminated indication pattern onto the plane of interest of an orthopedic plate attached to the distal end of a plate holder, in accordance with another representative embodiment of the present disclosure.

Another embodiment of the implant alignment device 110 and implantation system 114 of the present disclosure is shown in FIG. 5, in which the implant alignment device 110 includes multiple light sources 120 that together project an illuminated indication pattern 128 comprising multiple light lines 126, 127 that are arranged in the form a crosshair. In this embodiment the mounting interface 130 can comprise a block-shaped body 132 that encircles the elongate rod 168 of the plate holder 160 at a location spaced from the distal end 162, but below the handgrip 174 and the actuator handle 176 located at the proximal end of the plate holder 160. The body 132 can serve as an enclosure that supports four light sources 120, such as lasers or highly-focused LED's, that are equally spaced into each of the four quadrants surrounding the elongate rod 168, with each of the light sources 120 projecting a shaped beam of light 124 downward onto the plane 152 of the orthopedic plate 140 to create primary light lines 126 and secondary light lines 127 on the body of the patient, with the primary light lines being aligned with the primary axis of interest 150 of the orthopedic plate 140, and the secondary light lines 127 being aligned with the secondary axis of interest 154 that is perpendicular to the primary axis of interest 150. Both the primary light lines 126 and secondary light lines 127 can intersect with the distal end 162 of the plate holder 160.

In one embodiment the body 132 of the mounting interface 130 can also include an adjustment member 134, such as a blunt-tipped screw mounted within a threaded hole that intersects with the central aperture. The fastening member 134 can be used to secure the mounting interface 130 to the elongate rod 168 when tight while permitting rotation around the rod when loose, thereby allowing the angular position of the implant alignment device 110 to be adjusted to align the illuminated indication pattern 128 with the axes of interest 150, 154 of the orthopedic plate 140.

In addition, in one aspect the laser or light for the secondary light lines 127 can be projected a shorter lateral distance from the plate holder 160 than the primary light lines 126, but still ranging from three inches to two feet or more in length. The length of the secondary light lines 127 could be, however, as long as desired. The secondary light lines 127 can provide the surgeon with a second check on the collinearity to the bone/body in the transverse plane. For example, a skilled surgeon would expect the secondary light lines 127 to be orthogonal to the limb or body edge. If the secondary light lines 127 intersect the edge of the limb or body at an angle that is not orthogonal, then the surgeon should question collinearity to the bone. Of course, each bone has a unique relationship to its respective surface anatomy, but surgeons can become experienced with the variations in surface anatomy from one location to another. They can then make accommodation based on experience as to whether the secondary light lines 127 is expected to be orthogonal to the edge of the limb or body when the primary light lines 126 are aligned with their designated reference markers.

Example 2

Figure 6:
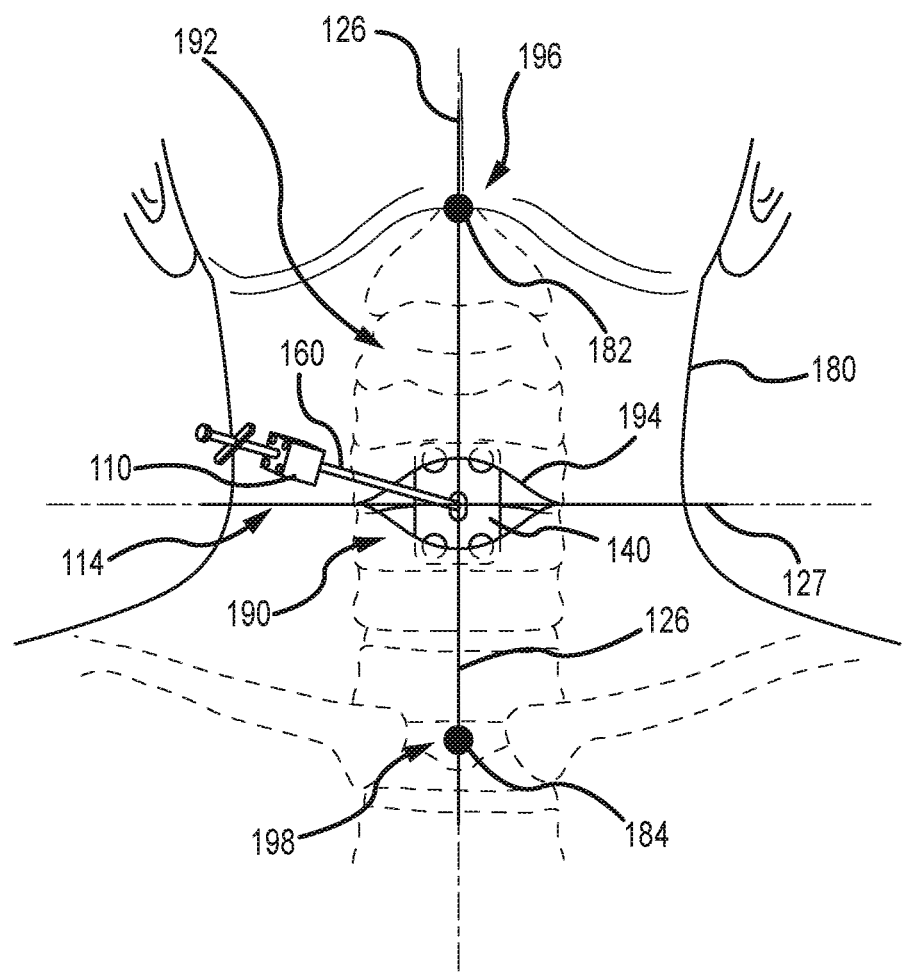
FIG. 6 is a schematic diagram illustrating the application of the implant alignment device of FIG. 5 in aligning an orthopedic plate to the cervical spine of a patient, in accordance with another representative embodiment of the present disclosure.

FIG. 6 provides a diagram of an example of the use of the implant alignment device 110 and implantation system 114 of the present disclosure to align a cervical plate to the cervical spine 190. As shown in the drawing, during an anterior cervical discectomy and fusion (ACDF), the surgeon is visualizing a limited region of the cervical spine 190 through a small incision 194 in the neck 180. The cervical spine anatomy 192 is significantly deeper in the neck 180 and it is difficult to judge alignment based solely on the limited exposure. In this scenario, after stabilizing the head in an appropriate position to avoid bending and rotation, the surgeon could palpate and mark the chin 196 or the center of the forehead as the cranial center position, thereby establishing a first superficial anatomic landmark or reference marker 182. Next, the surgeon could palpate and mark the sternal notch 198 or the xiphoid as the caudal center position, thereby establishing a second superficial anatomic landmark or reference marker 184.

The surgeon or an assisting medical professional can also attach the orthopedic plate 140 to the distal end of the plate holder 160 and activate the light sources 120 of the implant alignment device 110 to verify that the illuminated indication pattern 128 is aligned with the primary axis of interest 150 of the orthopedic plate 140. In situations where the illuminated indication pattern 128 is not aligned with the primary axis of interest 150 and angular adjustment of the implant alignment device 110 relative to the bone holder 160 is possible, the angular position of the implant alignment device 110 can be adjusted to bring the illuminated indication pattern 128 into alignment with the primary axis of interest 150.

During surgery the distal end of the implantation system 114 can then be used to insert the plate 140 into the incision 194 and adjacent the desired bone attachment site, and the light sources 120 can be activated to project the illuminated indication pattern 128 with primary light lines 126 that extend from the distal end of the plate holder 160 in opposite directions to both of the reference markers 182, 184 that have been marked on the exterior of the patient. The surgeon can then align the primary light lines 126 emitted from the implant alignment device 110 to these marked anatomic structures 196 and 198, after which he or she can insert two temporary stabilizing pins into the cervical plate 140 while closely observing that the primary light lines 126 do not deviate from the strategically placed marks 182, 184. At the same time the surgeon can observe the relationship between the secondary light lines 127 and the visible edges of the neck 180 to verify the collinearity of the cervical plate 140 to the spine 190 in the transverse direction.

Once the surgeon has confidently positioned the implant 140 on the bone (that has limited visualization) with the primary light lines 126 collinear to the surface anatomy, then the surgeon can permanently fixate the implant 140 to the bone. He or she would place permanent screws through the plate 140 to stably fix the plate in the desired collinear position. Since the primary light lines 126 are long, small deviations of the plate will be easily noticed by an exaggerated deviation of the light lines at their extremes near the reference markers 182, 184. Therefore, anatomic points that are farther from the bone attachment site under the incision 194 will provide better accuracy.

It will be appreciated that during the fixation process (e.g., when screws are being placed through the holes of a plate to attach the plate to the bone), the implant 140 can shift. The present disclosure will also assist the surgeon in assessing whether an implant has shifted during the fixation process. If the cross-hair lines (primary light lines 126 or secondary light lines 127) shift from the intended surface anatomy during the fixation process, then the surgeon would know that they would need to re-adjust the implant 140 to the desired position and then re-apply fixation screws. Once the implant 140 has been confidently attached collinear to the bone, then the implantation system 114 can be detached from the implant 140 and removed from the patient. This feature allows the surgeon to collinearly attach the plate to the bone in "real time."

Example 3

Figure 7:
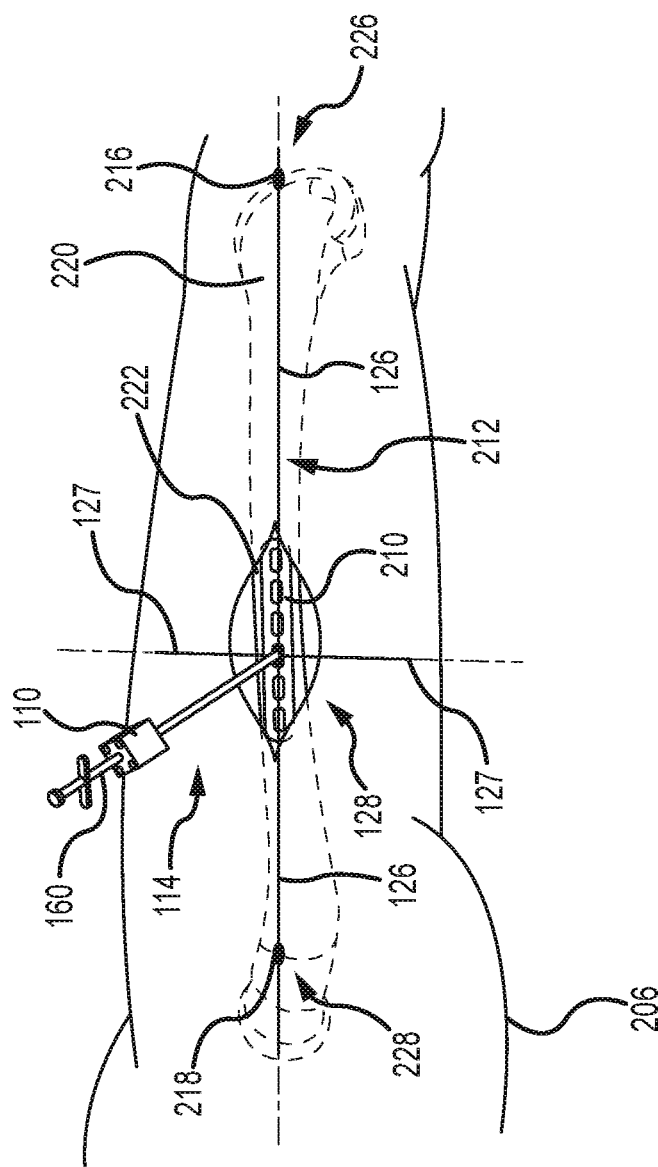
FIG. 7 is a schematic diagram illustrating the application of the implant alignment device of FIG. 5 in aligning an orthopedic plate to the lateral femur of a patient, in accordance with another representative embodiment of the present disclosure.

FIG. 7 illustrates another embodiment of the implant alignment device 110 and implantation system 114 of the present disclosure, as may be applied in the alignment of an orthopedic plate, such as lateral femoral fixation plate 210, to the lateral femur 220 of a patient. Since the desired anatomic landmarks for this surgery are generally palpable through the ski, the surgeon could palpate and mark the anterior distal femoral condyle 226, thereby establishing a first superficial anatomic landmark or reference marker 216. Next, the surgeon could palpate and mark the anterior one-third of the greater trochanter 228, thereby establishing a second superficial anatomic landmark or reference marker 218. In this scenario the alignment between the reference markers can appear off-center due to the bow-shape of the femur 220.

Prior to inserting the orthopedic plate 210 into the patient, the surgeon or an assisting medical professional can first attach the orthopedic plate 210 to the distal end of the plate holder 160 and activate the light sources 120 of the implant alignment device 110 to verify that the primary light lines 126 of the illuminated indication pattern 128 are aligned with the primary axis of interest 212 of the orthopedic plate 210. In situations where the illuminated indication pattern 128 is not aligned with the primary axis of interest 212 and angular adjustment of the implant alignment device 110 relative to the bone holder 160 is possible, the angular position of the implant alignment device 110 can be adjusted to bring the primary light lines 126 into alignment with the primary axis of interest 212 prior to inserting the plate 210 into the incision 222 and moving it toward the bone attachment site.

As shown in the drawing, a limited exposure of the lateral femur 220 can be provided through a standard direct lateral incision 222 into the thigh 206, allowing the plate 210 to be placed onto the lateral femur 220. The light sources 120 can be activated to project the illuminated indication pattern 128 with primary light lines 126 that extend from the distal end of the plate holder 160 in opposite directions to both of the reference markers 216, 218 that have been marked on the exterior of the leg of the patient. Once the primary light lines 126 are aligned according the desired superficial anatomic landmarks or reference marker 216, 218 and the secondary light lines 127 are aligned perpendicular to the long axis of the leg, the surgeon places temporary fixation (k-wires) and then permanent screw fixation. As long as the illuminated indication pattern 128 does not deviate from the reference markers 216, 218, the surgeon can be confident that the lateral femoral plate 210 was applied collinear to the lateral femur 220.

Example 4

Figure 8:
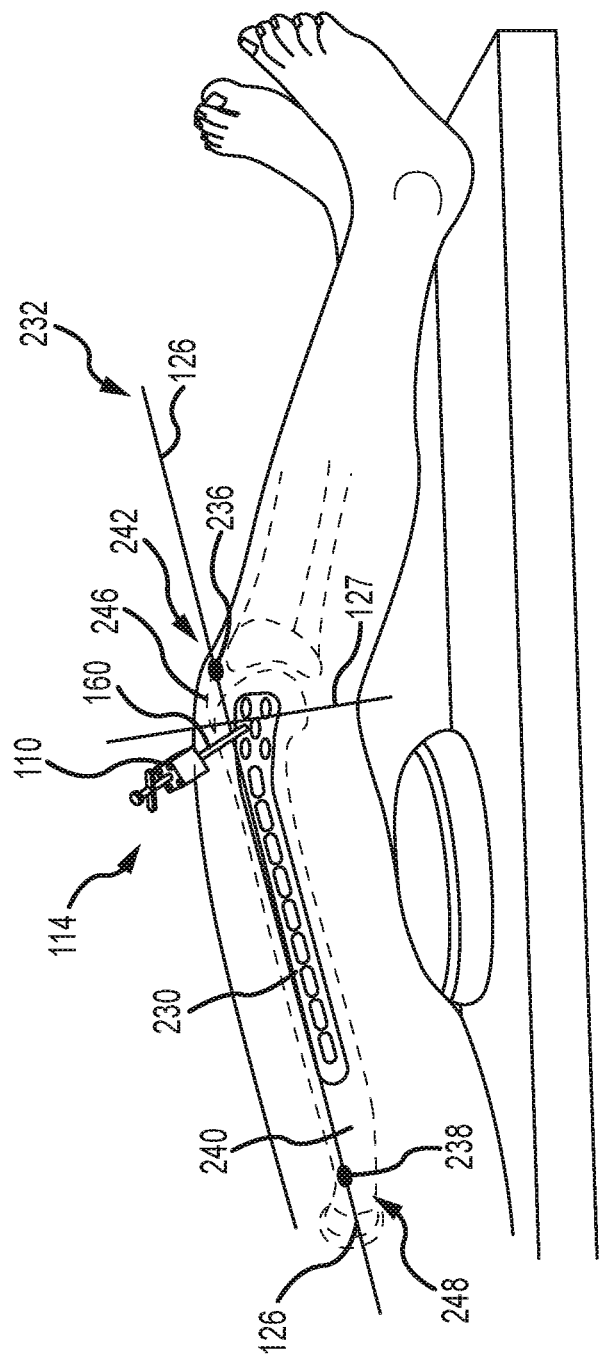
FIG. 8 is a schematic diagram illustrating the application of the implant alignment device of FIG. 5 in aligning an orthopedic plate to the distal femur of a patient, in accordance with another representative embodiment of the present disclosure.

FIG. 8 illustrates another embodiment of the implant alignment device 110 and implantation system 114 of the present disclosure, as may be applied in the alignment of a plate to the proximal femur 240 using a minimally invasive technique known to one skilled in the art. This minimally invasive approach is what differentiates this example from Example 3. As shown in FIG. 8, a small incision 242 is made over the lateral aspect of the distal femur 240. Then, the plate 230, such as a lateral femoral plate, is slid along a submuscular plane along the lateral thigh over the femur 240. The minimally invasive plate 230 used in this technique has a screw guide that is used to place locking screws through stab wounds in the skin into the plate; fixing the plate to the femur. Current application of the plate 230 along the lateral femur 240 can be tenuous as the surgeon does this solely by tactical sensation. During the sliding process, there is risk to neurovascular structures anterior and posterior to the femur 240 if the plate 230 slides off course. The method and system of the present disclosure, as provided in FIG. 8, may be used to guide the surgeon in sliding the minimally invasive plate 230 along the correct trajectory. For instance, the primary light lines 126 that extend from the distal end of the plate holder 160 in opposite directions can be aligned with the superficial anatomic landmarks or reference markers 236, 238 that have been established on the anterior distal femoral condyle 246 and the anterior one-third of the greater trochanter 248, respectively, while the secondary light lines 127 can be maintained orthogonal to long axis of the leg. This method can help guide the orthopedic plate 230 along a safe trajectory in the submuscular plane to the bone attachment site.

It will be further appreciated that the surgical implant alignment device of the present disclosure can provide additional features and benefits beyond the initial alignment of the implant. For instance, when the first screw is placed into position within an aligned orthopedic fixation plate, it will many times shift the position of the plate. This will be seen as a change in the angle and/or position of the projected laser or light lines. The length of the light lines amplifies the movement of the plate imparted by positioning the screw, thus making potential misalignment detectable. Once a deviation from true alignment or collinearity has detected with the first screw in position, the handle of the plate holder may be rotated to the correct orientation and the second screw inserted. With two screws, proper alignment can be confirmed and the position of the orthopedic plate will remain stable for the insertion of the final two screws.

Other benefits of the implant alignment device of the present disclosure include the reduction in a patient's exposure to radiation, since common fixation procedures require the use of X-rays are used to confirm the position of the implant fixation plate, sometimes multiple times during the procedure. The use of the implant alignment device to properly orient the implant during initial positioning, as well as to correct any shifts caused by screw insertions, can substantially reduce the need for as many X-rays as would otherwise be required, thus reducing the patient's radiation exposure.

Superficial Anatomic Landmark Combinations

Figure 9A:
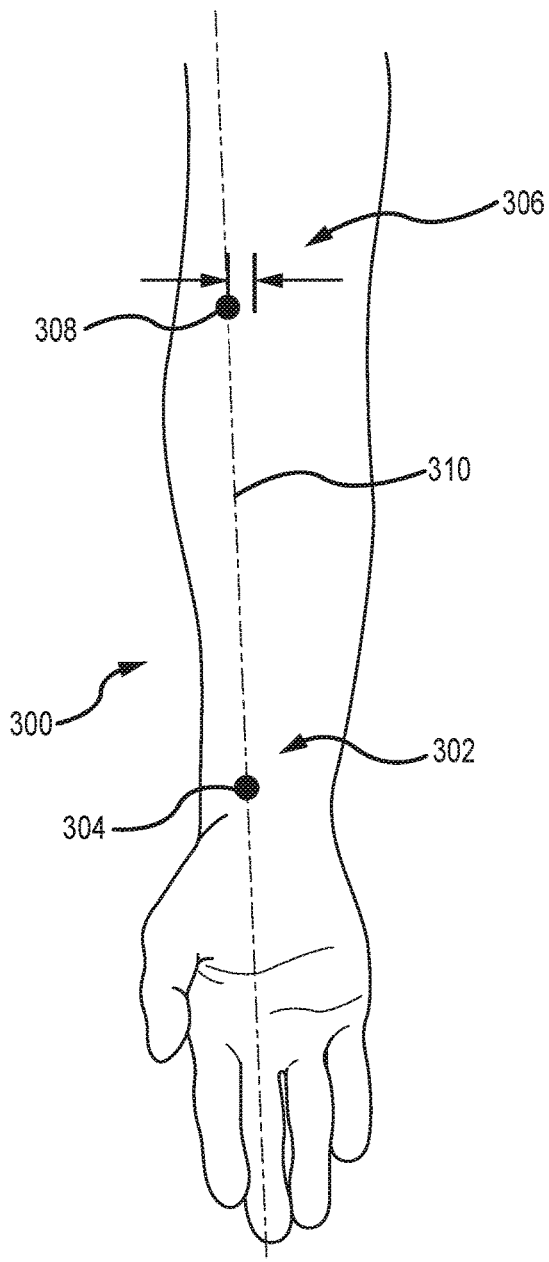
FIGS. 9A-9B are lower arm anterior surface feature and anatomic diagrams, respectively, that illustrate a combination of superficial anatomic landmarks that can be used to align an orthopedic implant to the anterior radius of a patient, in accordance with another representative embodiment of the present disclosure.
Figure 9B:
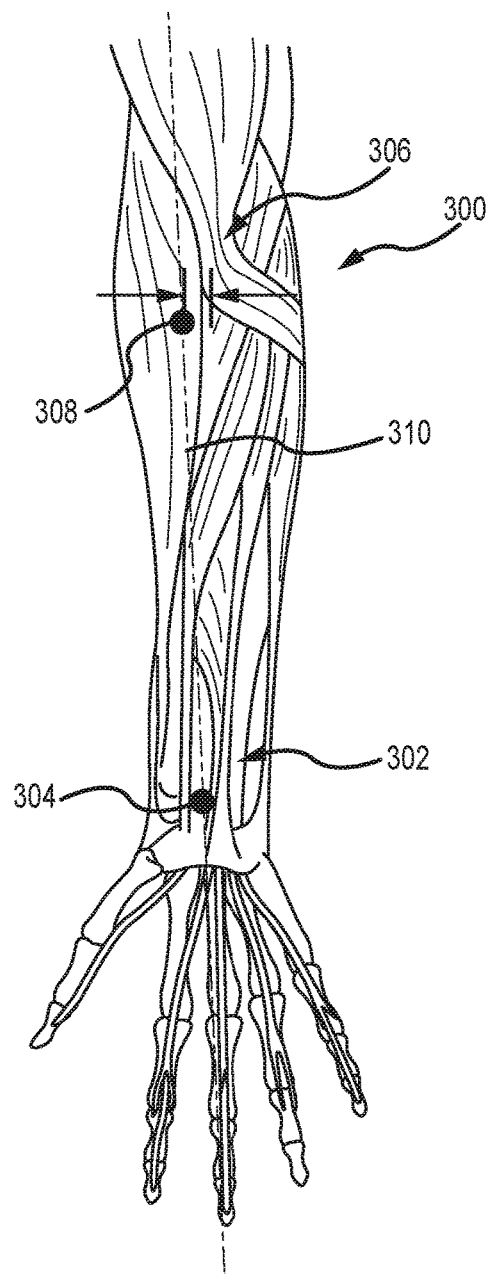

In addition to the detailed examples illustrated and described above, the inventor has also discovered several new superficial anatomic landmark combinations that can be established and referenced in different orthopedic plate-setting surgeries. For example, as illustrated in FIGS. 9A-9B, when setting a plate on the anterior radius 300 of a patient, the flexor carpii radialis tendon 302 can be designated as the location for a first reference marker 304, and a 1 cm radial offset 307 from the insertion of the biceps brachii muscle 306 can be designated as the marking site for a second reference marker 308. During surgery, the primary axis of interest of an orthopedic plate can then be aligned with the imaginary reference line 310 drawn between the two reference markers 304, 308 using the implant alignment device and/or and implantation system of the present disclosure, as described above, to establish accurate collinearity between the implant and the longitudinal axis of the radius.

Figures 10A, 10B:
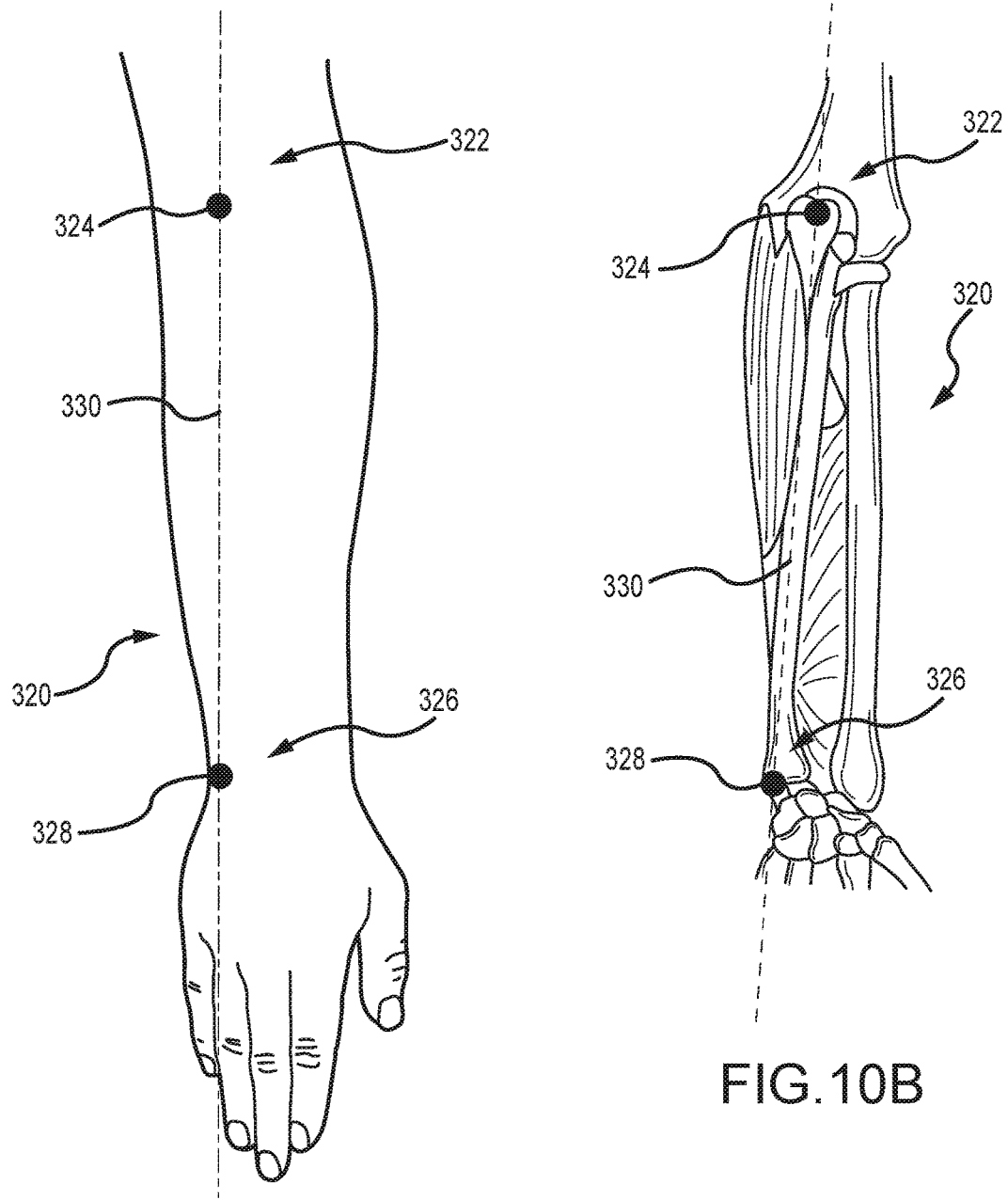
FIGS. 10A-10B are lower arm posterior surface feature and anatomic diagrams, respectively, that illustrate a combination of superficial anatomic landmarks that can be used to align an orthopedic implant to the posterior ulna of a patient, in accordance with another representative embodiment of the present disclosure.

In another embodiment of the present disclosure illustrated in FIGS. 10A-10B, when setting a plate on the posterior ulna 320 of a patient, the olecranon 322 can be designated as the location for a first reference marker 324, and the styloid process of the ulna 326 can be designated as the marking site for a second reference marker 328. During surgery, the primary axis of interest of an orthopedic plate can then be aligned with the imaginary reference line 330 drawn between the two reference markers 324, 328 using the implant alignment device and/or and implantation system of the present disclosure, as described above, to establish accurate collinearity between the implant and the longitudinal axis of the ulna.

Figure 11:
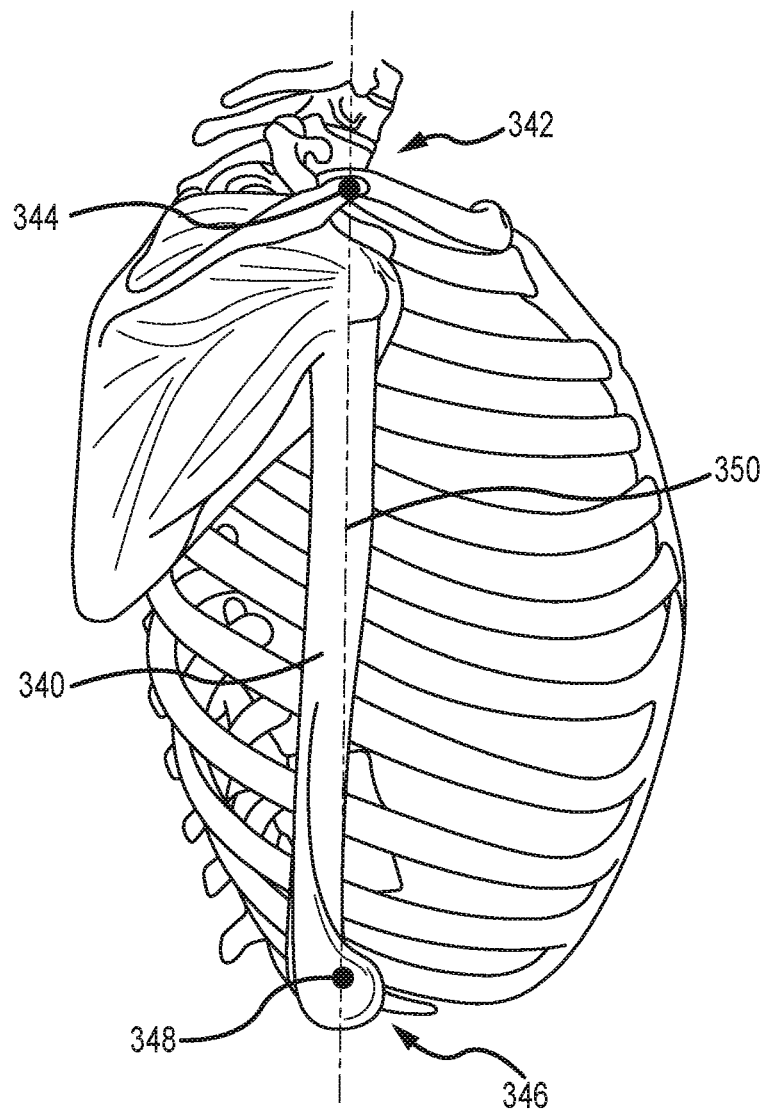
FIG. 11 is an anatomic diagram that illustrate a combination of superficial anatomic landmarks that can be used to align an orthopedic implant to the lateral humerus of a patient, in accordance with another representative embodiment of the present disclosure.

In another embodiment of the present disclosure illustrated in FIG. 11, when setting a plate on the lateral humerus 340 of a patient, the center of the lateral acromion 342 can be designated as the location for a first reference marker 344, and the lateral humeral condyle 346 can be designated as the marking site for a second reference marker 348. During surgery, the primary axis of interest of an orthopedic plate can then be aligned with the imaginary reference line 350 drawn between the two reference markers 344, 348 using the implant alignment device and/or and implantation system of the present disclosure, as described above, to establish accurate collinearity between the implant and the longitudinal axis of the humerus.

Figures 12A, 12B:
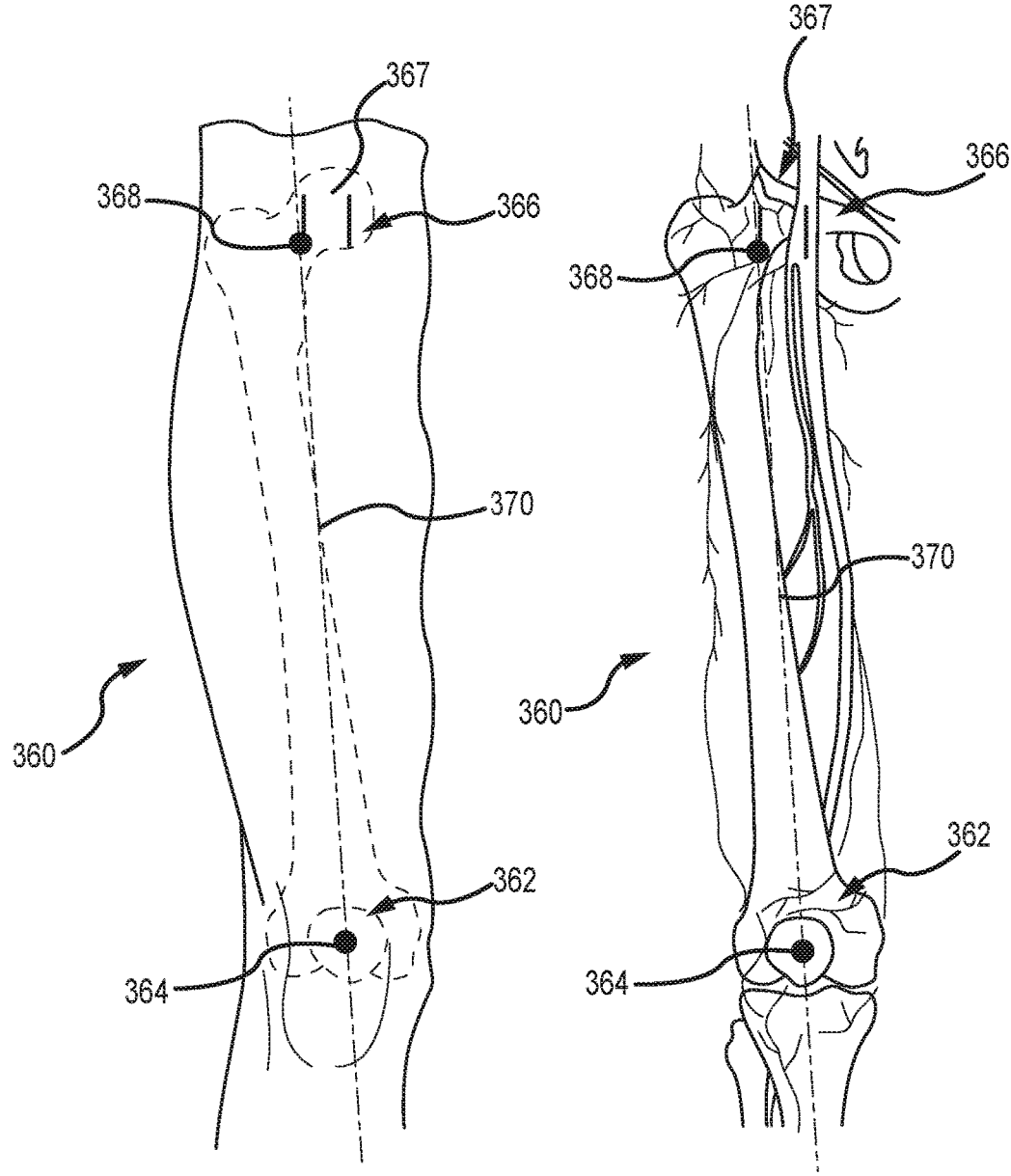
FIGS. 12A-12B are upper leg anterior surface feature and anatomic diagrams, respectively, that illustrate a combination of superficial anatomic landmarks that can be used to align an orthopedic implant to the anterior femur of a patient, in accordance with another representative embodiment of the present disclosure.

In another embodiment of the present disclosure illustrated in FIGS. 12A-12B, when setting a plate on the anterior femur 360 of a patient, the center of the superior pole of the patella 362 can be designated as the location for a first reference marker 364, and a 2 cm lateral offset 367 from the deep femoral artery pulse 366 can be designated as the marking site for a second reference marker 368. During surgery, the primary axis of interest of an orthopedic plate can then be aligned with the imaginary reference line 370 drawn between the two reference markers 364, 368 using the implant alignment device and/or and implantation system of the present disclosure, as described above, to establish accurate collinearity between the implant and the longitudinal axis of the femur.

Figure 13A:
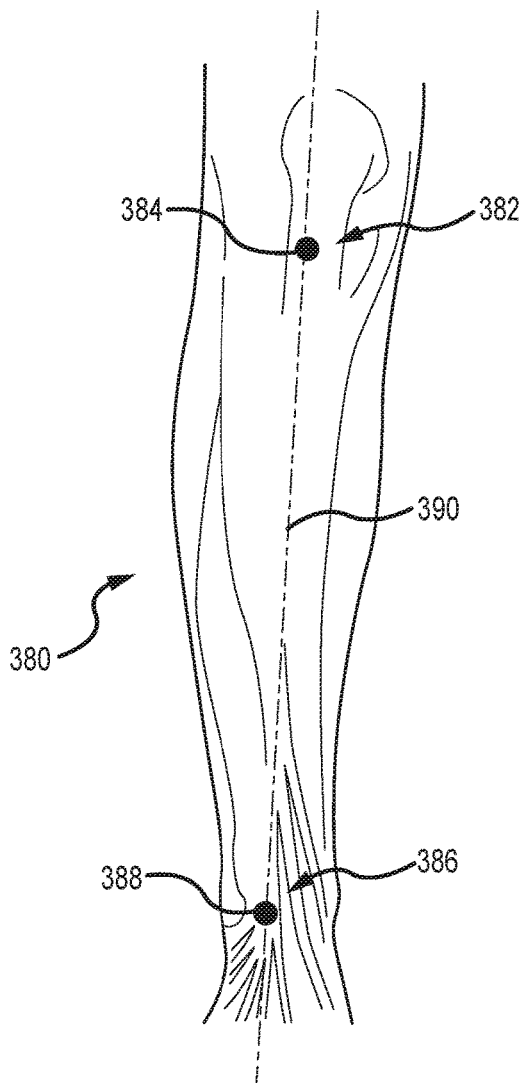
FIGS. 13A-13B are lower leg anterior surface feature and anatomic diagrams, respectively, that illustrate a combination of superficial anatomic landmarks that can be used to align an orthopedic implant to the anterior tibia of a patient, in accordance with another representative embodiment of the present disclosure.
Figure 13B:
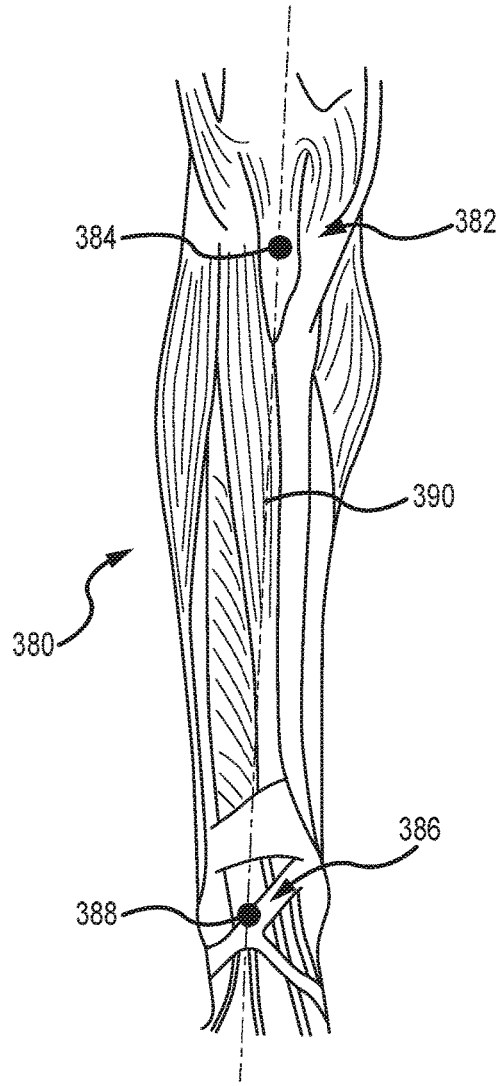

In another embodiment of the present disclosure illustrated in FIGS. 13A-13B, when setting a plate on the anterior tibia 380 of a patient, the tuberosity of the tibia 382 can be designated as the location for a first reference marker 384, and the extensor digitorum tendon 386 can be designated as the marking site for a second reference marker 388. During surgery, the primary axis of interest of an orthopedic plate can then be aligned with the imaginary reference line 390 drawn between the two reference markers 384, 388 using the implant alignment device and/or and implantation system of the present disclosure, as described above, to establish accurate collinearity between the implant and the longitudinal axis of the tibia.

Figures 14A, 14B:
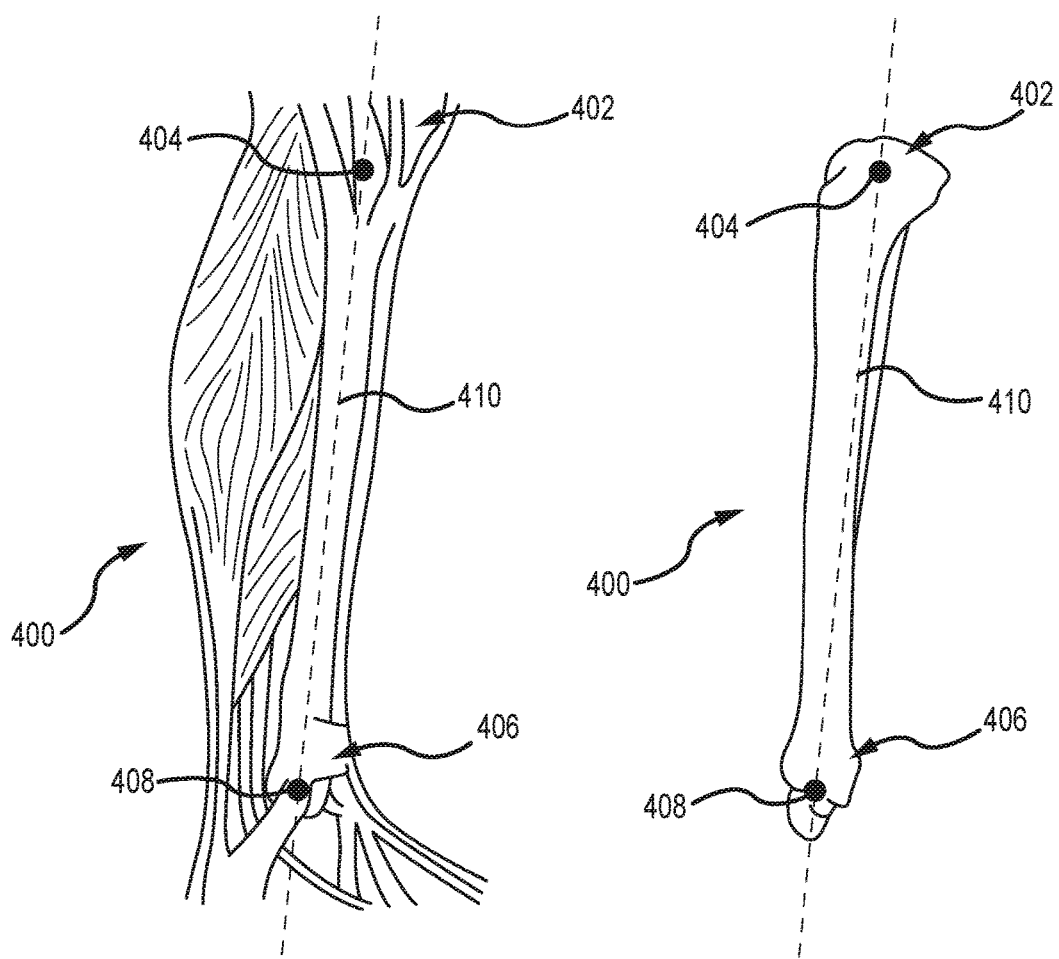
FIGS. 14A-14B are lower leg medial anatomic diagrams that illustrate a combination of superficial anatomic landmarks that can be used to align an orthopedic implant to the medial tibia of a patient, in accordance with another representative embodiment of the present disclosure.

In another embodiment of the present disclosure illustrated in FIGS. 14A-14B, when setting a plate on the medial tibia 400 of a patient, the medial femoral condyle of the tibia 402 can be designated as the location for a first reference marker 404, and the medial malleolus of the tibia 406 can be designated as the marking site for a second reference marker 408. During surgery, the primary axis of interest of an orthopedic plate can then be aligned with the imaginary reference line 410 drawn between the two reference markers 404, 408 using the implant alignment device and/or and implantation system of the present disclosure, as described above, to establish accurate collinearity between the implant and the longitudinal axis of the tibia.

Figures 15A, 15B:
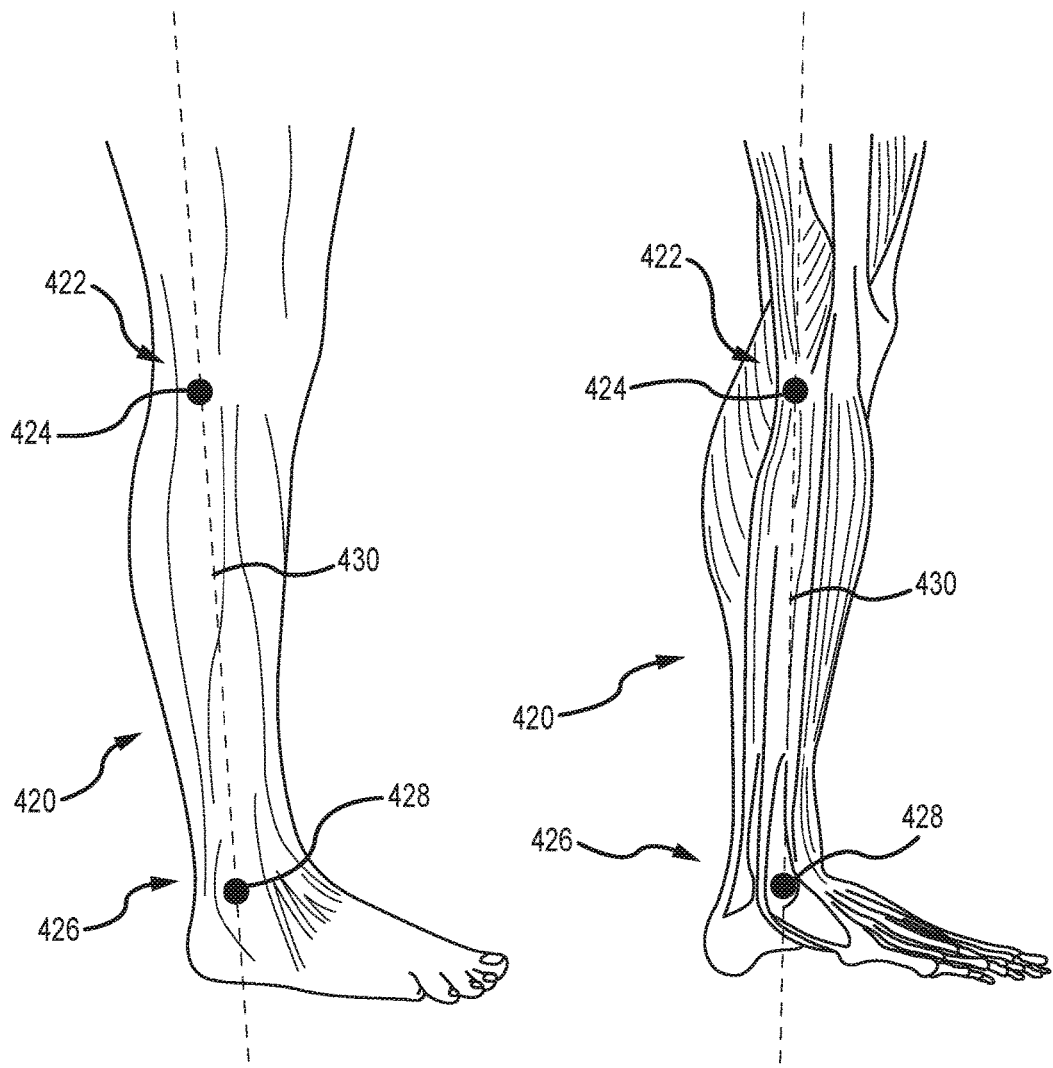
FIGS. 15A-15B are lower leg anterior surface feature and anatomic diagrams, respectively, that illustrate a combination of superficial anatomic landmarks that can be used to align an orthopedic implant to the fibula of a patient, in accordance with another representative embodiment of the present disclosure.

In another embodiment of the present disclosure illustrated in FIGS. 15A-15B, when setting a plate on the lateral fibula 420 of a patient, the head of the fibula 422 can be designated as the location for a first reference marker 424, and the lateral malleolus of the fibula 426 can be designated as the marking site for a second reference marker 428. During surgery, the primary axis of interest of an orthopedic plate can then be aligned with the imaginary reference line 430 drawn between the two reference markers 424, 428 using the implant alignment device and/or and implantation system of the present disclosure, as described above, to establish accurate collinearity between the implant and the longitudinal axis of the fibula.

As indicated above, the invention has been described herein in terms of preferred embodiments and methodologies considered by the inventor to represent the best mode of carrying out the invention. It will be understood by the skilled artisan, however, that a wide range of additions, deletions, and modifications, both subtle and gross, may be made to the illustrated and exemplary embodiments of the implant alignment device without departing from the spirit and scope of the invention. For example, while a principle use of the surgical implant alignment device of the present disclosure is the application in surgery on human patients, the alignment device is also suitable for application during surgery on any animal, including but not limited to dogs, cats, horses, cattle, goats, sheep, cattle, pigs, as well as other animals such as birds and lizards. These and other revisions might be made by those of skill in the art without departing from the spirit and scope of the invention that is constrained only by the following claims.

What is claimed is:

1. An alignment device securable to an orthopedic plate holder for aligning an orthopedic plate with a bone attachment site of a patient using at least one superficial anatomic landmark on an exterior of the patient and remote from the bone attachment site, with the orthopedic plate holder having a distal end that is releasably attachable to an orthopedic plate in a fixed angular position to define a plane of interest and a predetermined axis of interest within the plane of interest, and a proximal end adapted for holding by a medical professional, the alignment device comprising:

at least one light source configured to project an illuminated indication pattern onto the plane of interest of the orthopedic plate and aligned with the predetermined axis of interest of the orthopedic plate; and a mounting interface configured to secure the light source lo the orthopedic plate holder in a location spaced from the distal end, in a fixed angular position relative to the plate holder, and to maintain an angular relationship between the light source and the orthopedic plate as the distal end of the orthopedic plate holder is inserted into the patient by the medical professional and moved toward a bone attachment site that is at least partially out-of-view of the medical professional, wherein the illuminated indication pattern extends a sufficient lateral distance away from the orthopedic plate holder and has a substantially constant brightness along a length thereof to allow the medical professional to align the axis of interest of the orthopedic plate with the out-of-view bone attachment site using the at least one superficial anatomic landmark.

2. The alignment device of claim 1, wherein the illuminated indication pattern further comprises at least one light line that is aligned with the predetermined axis of interest of the orthopedic plate, intersects the distal end of the orthopedic plate holder, and projects a lateral distance from the orthopedic plate holder at least twice a length of the orthopedic plate holder.

3. The alignment device of claim 1, wherein the illuminated indication pattern further comprises a crosshair pattern formed by oppositely-projected primary light lines that are aligned with the predetermined axis of interest of the orthopedic plate and oppositely-projected secondary light lines that are transverse lo the predetermined axis of interest.

4. The alignment device of claim 3, wherein each of the primary light lines and the secondary light lines intersect the distal end of the orthopedic plate holder.

5. The alignment device of claim 3, wherein a projected lateral distance of each of the primary light lines from the orthopedic plate holder is at least 24 inches.

6. The alignment device of claim 3, wherein a projected lateral distance of each of the primary light lines from the orthopedic plate holder is at least 36 inches.

7. The alignment device of claim 3, wherein a projected lateral distance of each of the primary light lines from the orthopedic plate holder is at least twice a length of the orthopedic plate holder.

8. The alignment device of claim 1, wherein the at least one light source further comprises a plurality of light sources located at spaced angular positions around an axis of the orthopedic plate holder and configured to project a portion of the illuminated indication pattern.

9. The alignment device of claim 8, wherein each of the plurality of light sources projects a single light line defining a portion of the illuminated indication pattern.

10. The alignment device of claim 8, wherein at least one light source of the plurality of light sources projects a plurality of light lines defining a portion of the illuminated indication pattern.

11. The alignment device of claim 1, wherein the mounting interface is angularly adjustable relative to a longitudinal centerline axis of the orthopedic plate holder.

12. The alignment device of claim 1, wherein the mounting interface is integrally formed with the orthopedic plate holder.

13. The alignment device of claim 1, wherein the orthopedic plate holder further comprises a hollow elongate rod having an actuator mechanism disposed therein.

14. An implant placement and alignment system for positioning and aligning, by a medical professional, an orthopedic implant to a bone attachment site of a patient using a plurality of superficial anatomic landmarks on an exterior of the patient and remote from the bone attachment site, the system comprising:
  an implantation tool having a distal end that is releasably attachable to an orthopedic implant in a fixed angular position to define a plane of interest of the orthopedic implant and a predetermined axis of interest of the orthopedic implant within the plane of interest, and a proximal end adapted for holding by the medical professional; and
  an alignment device securable to the implantation tool for aligning the predetermined axis of interest of the orthopedic implant with the bone attachment site, the alignment device comprising:
  at least one light source configured to project an illuminated indication pattern onto the plane of interest of the orthopedic implant and aligned with the predetermined axis of interest of the orthopedic implant; and
  a mounting interface configured to secure the light source to the implantation tool in a location spaced from the distal end, in a fixed angular position relative to the implantation tool, and to maintain an angular relationship between the light source and the orthopedic plate as the distal end of the implantation tool is inserted into the patient by the medical professional and moved toward the bone attachment site that is at least partially out-of-view of the medical professional, wherein
  the illuminated indication pattern extends a sufficient lateral distance away from the implantation tool to allow the medical professional to align the axis of interest of the orthopedic plate with the out-of-view bone attachment site using the plurality of superficial anatomic landmarks, and wherein
  the illuminated indication pattern further comprises a crosshair pattern formed by oppositely-projected primary light lines that are aligned with the predetermined axis of interest of the orthopedic plate and oppositely-projected secondary light lines that are transverse to the predetermined axis of interest.

15. The alignment device of claim 14, wherein each of the primary light lines and the secondary light lines intersect the distal end of the orthopedic plate holder.

16. The alignment device of claim 14, wherein each of the primary light lines is projected a lateral distance from the implantation tool of at least 24 inches and has a substantially constant brightness along a length thereof.

17. A method for mounting an orthopedic plate to a bone attachment site of a patient using a plate holder having a proximal end adapted for holding by a medical professional, a distal end, an orthopedic plate secured to the distal end in a fixed angular position to define a plane of interest of the orthopedic plate and a predetermined axis of interest of the orthopedic plate within the plane of interest, and an alignment device having a light source secured to the plate holder in a location spaced from the distal end and configured to illuminate at least one superficial anatomic landmark on an exterior of the patient and remote from the bone attachment site, the method comprising:
  using the light source of the alignment device to project an illuminated indication pattern onto the plane of interest of the orthopedic plate and aligned with the predetermined axis of interest of the orthopedic plate;
  moving the plate holder to insert the orthopedic plate into the patient and adjacent to a bone attachment site that is out-of-view of the medical professional;
  rotating the plate holder to align the illuminated indication pattern with the at least one superficial anatomic landmark that is visible to the medical professional on an outer surface of the patient, thereby positioning the orthopedic plate in a desired collinear orientation relative to the out-of-view bone attachment site;
  attaching the orthopedic plate to the bone attachment site; and
  releasing the plate holder from the orthopedic plate and removing the plate holder from the patient.

18. The method of claim 17, further comprising rotating the plate holder to align the illuminated indication pattern with a pair of superficial anatomic landmarks located on opposite sides of the bone attachment site.

19. The method of claim 18, wherein the bone attachment site is located on an anterior humerus of the patient and the pair of superficial anatomic landmarks comprises a center of an acromion and a tendon of a biceps brachii of the patient, respectively.

20. The method of claim 18, wherein the bone attachment site is located on a cervical spine of the patient and the pair of superficial anatomic landmarks comprises a center of a forehead and a sternal notch of the patient, respectively.

21. The method of claim 18, wherein the bone attachment site is located on a lateral femur of the patient and the pair of superficial anatomic landmarks comprises an anterior distal femoral condyle and an anterior one-third of a greater trochanter of the patient, respectively.

22. The method of claim 18, wherein the bone attachment site is located on a distal femur of the patient and the pair of superficial anatomic landmarks comprises an anterior distal femoral condyle and an anterior one-third of a greater trochanter of the patient, respectively.

23. The method of claim 18, wherein the bone attachment site is located on an anterior radius of the patient and the pair of superficial anatomic landmarks comprises a flexor carpii radialis tendon and a 1 cm radial offset from an insertion of a biceps brachii muscle of the patient, respectively.

24. The method of claim 18, wherein the bone attachment site is located on an ulna of the patient and the pair of superficial anatomic landmarks comprises an olecranon and a styloid process of the ulna, respectively.

25. The method of claim 18, wherein the bone attachment site is located on a lateral humerus of the patient and the pair of superficial anatomic landmarks comprises a center of a lateral acromion and a lateral humeral condyle of the patient, respectively.

26. The method of claim 18, wherein the bone attachment site is located on an anterior femur of the patient and the pair of superficial anatomic landmarks comprises a 2 cm lateral offset from a femoral artery pulse and a center of a superior pole of a patella of the patient, respectively.

27. The method of claim 18, wherein the bone attachment site is located on an anterior tibia and the pair of superficial anatomic landmarks comprises a tuberosity of a tibia and a extensor digitorum tendon of the patient, respectively.

28. The method of claim 18, wherein the bone attachment site is located on a medial tibia of the patient, and the pair of superficial anatomic landmarks comprises a center of medial femoral condyle of a tibia and a medial malleolus of a tibia, respectively.

29. The method of claim 18, wherein the bone attachment site is located on a fibula of the patient and the pair of superficial anatomic landmarks comprises a head of the fibula and a lateral malleolus of the fibula, respectively.

30. The method of claim 17, further comprising rotating the plate holder to align the illuminated indication pattern with a pair of superficial anatomic landmarks located on a same side of the bone attachment site.

\* \* \* \* \*